(12) United States Patent
Bettuchi

(10) Patent No.: US 8,206,357 B2
(45) Date of Patent: Jun. 26, 2012

(54) ARTICULATING SURGICAL PORTAL APPARATUS WITH SPRING

(75) Inventor: Michael J. Bettuchi, Middletown, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 216 days.

(21) Appl. No.: 12/701,787

(22) Filed: Feb. 8, 2010

(65) Prior Publication Data

US 2010/0249708 A1    Sep. 30, 2010

Related U.S. Application Data

(60) Provisional application No. 61/163,490, filed on Mar. 26, 2009.

(51) Int. Cl.
*A61M 5/00* (2006.01)

(52) U.S. Cl. ......... 604/167.01; 604/167.02; 604/167.03; 604/167.06

(58) Field of Classification Search ............... 604/167.01–167.03, 167.06, 256
See application file for complete search history.

(56) References Cited

U.S. PATENT DOCUMENTS

| | | | |
|---|---|---|---|
| 3,421,509 A | 1/1969 | Fiore | |
| 3,565,078 A | 2/1971 | Vailliancourt et al. | |
| 3,853,127 A | 12/1974 | Spademan | |
| 3,907,310 A | 9/1975 | Dufour | |
| 3,994,287 A | 11/1976 | Turp et al. | |
| 4,000,739 A | 1/1977 | Stevens | |
| 4,112,932 A | 9/1978 | Chiulli | |
| 4,173,350 A | 11/1979 | Sieghartner | |
| 4,177,814 A | 12/1979 | Knepshield et al. | |
| 4,177,997 A | 12/1979 | Cartwright | |
| 4,240,335 A | 12/1980 | Stucka et al. | |
| 4,240,411 A | 12/1980 | Hosono | |
| 4,311,315 A | 1/1982 | Kronenberg | |
| 4,334,688 A | 6/1982 | Spargo et al. | |
| 4,338,689 A | 7/1982 | Zieg | |
| 4,383,692 A | 5/1983 | Proctor | |
| 4,386,756 A | 6/1983 | Muchow | |
| 4,387,879 A | 6/1983 | Tauschinski | |
| 4,430,081 A | 2/1984 | Timmermans | |
| 4,447,237 A | 5/1984 | Frisch et al. | |
| 4,448,449 A | 5/1984 | Halling et al. | |
| 4,464,178 A | 8/1984 | Dalton | |

(Continued)

FOREIGN PATENT DOCUMENTS

DE    1 893 771 U    5/1964

(Continued)

OTHER PUBLICATIONS

European Search Report for EP 10 25 0573 date of completion is Jun. 29, 2010 (3 pages).

(Continued)

*Primary Examiner* — Laura Bouchelle

(57) ABSTRACT

A surgical portal apparatus is provided which includes a housing and a portal member. The portal member is connected to the housing which extends therefrom. The portal member has a longitudinal axis which includes a longitudinal passageway for permitting a surgical object to pass therethrough. A seal mount is mounted to the housing and has an internal seal adapted to establish a substantial sealed relation with the surgical object, the seal mount adapted to articulate relative to the housing between a first position relative to the housing and at least one second position relative to the housing, the seal mount being normally biased toward the first position.

16 Claims, 5 Drawing Sheets

U.S. PATENT DOCUMENTS

| | | | |
|---|---|---|---|
| 4,553,760 A | 11/1985 | Reed et al. | |
| 4,588,195 A | 5/1986 | Antonini et al. | |
| 4,601,710 A | 7/1986 | Moll | |
| 4,626,245 A | 12/1986 | Weinstein | |
| 4,641,842 A | 2/1987 | Kataoka | |
| 4,654,030 A | 3/1987 | Moll et al. | |
| 4,655,752 A | 4/1987 | Honkanen et al. | |
| 4,673,393 A | 6/1987 | Suzuki et al. | |
| 4,705,511 A | 11/1987 | Kocak | |
| 4,715,360 A | 12/1987 | Akui et al. | |
| 4,723,550 A | 2/1988 | Bales et al. | |
| 4,758,225 A | 7/1988 | Cox et al. | |
| 4,795,439 A | 1/1989 | Guest | |
| 4,842,591 A | 6/1989 | Luther | |
| 4,844,483 A | 7/1989 | Iijima et al. | |
| 4,844,484 A | 7/1989 | Antonini et al. | |
| 4,857,062 A | 8/1989 | Russell | |
| 4,869,717 A | 9/1989 | Adair | |
| 4,889,349 A | 12/1989 | Müller | |
| 4,909,798 A | 3/1990 | Fleischhacker et al. | |
| 4,912,287 A | 3/1990 | Ono et al. | |
| 4,932,633 A | 6/1990 | Johnson et al. | |
| 4,943,280 A | 7/1990 | Lander | |
| 4,960,412 A | 10/1990 | Fink | |
| 4,966,588 A | 10/1990 | Rayman et al. | |
| 4,998,740 A | 3/1991 | Tellier | |
| 5,000,745 A | 3/1991 | Guest et al. | |
| 5,002,557 A | 3/1991 | Hasson | |
| 5,015,000 A | 5/1991 | Perini | |
| 5,030,206 A | 7/1991 | Lander | |
| 5,038,756 A | 8/1991 | Kepley | |
| 5,041,095 A | 8/1991 | Littrell | |
| 5,053,014 A | 10/1991 | Van Heugten | |
| 5,053,016 A | 10/1991 | Lander | |
| 5,073,169 A | 12/1991 | Raiken | |
| 5,104,383 A | 4/1992 | Shichman | |
| 5,123,634 A | 6/1992 | Schwerdt | |
| 5,137,520 A | 8/1992 | Maxson et al. | |
| 5,154,701 A | 10/1992 | Cheer et al. | |
| 5,167,636 A | 12/1992 | Clement | |
| 5,180,373 A | 1/1993 | Green et al. | |
| 5,209,737 A | 5/1993 | Ritchart et al. | |
| 5,211,370 A | 5/1993 | Powers | |
| 5,226,891 A | 7/1993 | Bushatz et al. | |
| 5,273,545 A | 12/1993 | Hunt et al. | |
| 5,290,304 A | 3/1994 | Storace | |
| 5,299,813 A | 4/1994 | McKenna | |
| 5,300,036 A | 4/1994 | Mueller et al. | |
| 5,342,315 A | 8/1994 | Rowe et al. | |
| 5,350,364 A | 9/1994 | Stephens et al. | |
| 5,354,280 A | 10/1994 | Haber et al. | |
| 5,385,553 A | 1/1995 | Hart et al. | |
| 5,391,153 A | 2/1995 | Haber et al. | |
| 5,499,823 A | 3/1996 | Fukui | |
| 5,522,831 A | 6/1996 | Sleister et al. | |
| 5,603,702 A | 2/1997 | Smith et al. | |
| 5,613,954 A | 3/1997 | Nelson et al. | |
| 5,614,136 A | 3/1997 | Pepin et al. | |
| 5,685,854 A | 11/1997 | Green et al. | |
| 5,720,759 A | 2/1998 | Green et al. | |
| 5,779,697 A | 7/1998 | Glowa et al. | |
| 5,792,113 A | 8/1998 | Kramer et al. | |
| 5,820,600 A * | 10/1998 | Carlson et al. | 604/167.03 |
| 5,839,639 A | 11/1998 | Sauer et al. | |
| 5,957,888 A | 9/1999 | Hinchliffe | |
| 6,039,725 A | 3/2000 | Moenning et al. | |
| RE36,702 E | 5/2000 | Green et al. | |
| 6,086,603 A | 7/2000 | Termin et al. | |
| 6,113,106 A | 9/2000 | Dahlheimer | |
| 6,228,061 B1 | 5/2001 | Flatland et al. | |
| 6,231,565 B1 | 5/2001 | Tovey et al. | |
| 6,663,614 B1 | 12/2003 | Carter | |
| 7,037,344 B2 | 5/2006 | Kagan et al. | |
| 7,083,626 B2 | 8/2006 | Hart et al. | |
| 7,632,250 B2 | 12/2009 | Smith et al. | |
| 2004/0066008 A1 | 4/2004 | Smith | |
| 2004/0204682 A1 | 10/2004 | Smith | |
| 2005/0212221 A1 | 9/2005 | Smith et al. | |
| 2008/0149685 A1 | 6/2008 | Smith et al. | |
| 2008/0171987 A1 | 7/2008 | Franer et al. | |
| 2008/0249475 A1 | 10/2008 | Albrecht et al. | |
| 2009/0082720 A1 | 3/2009 | Smith | |
| 2009/0093752 A1 | 4/2009 | Richard et al. | |
| 2010/0100043 A1 | 4/2010 | Racenet | |

FOREIGN PATENT DOCUMENTS

| | | |
|---|---|---|
| DE | 3217118 CI | 8/1983 |
| EP | 0 029 864 B1 | 6/1981 |
| EP | 0 051 718 B1 | 5/1982 |
| EP | 0 113 520 A2 | 7/1984 |
| EP | 0 312 219 B1 | 4/1989 |
| EP | 1 707 133 A1 | 10/2006 |
| EP | 1 709 918 A1 | 10/2006 |
| EP | 1707133 | 10/2006 |
| EP | 2 042 114 A1 | 4/2009 |
| EP | 2 044 889 A1 | 4/2009 |
| EP | 2 087 846 A2 | 8/2009 |
| GB | 1482857 | 8/1977 |
| GB | 2298905 A | 9/1996 |
| WO | WO 93/04717 A1 | 3/1993 |
| WO | WO 97/42991 A1 | 11/1997 |
| WO | WO 98/53865 A1 | 12/1998 |
| WO | WO 02/41795 A2 | 5/2002 |
| WO | WO 03/094760 A2 | 11/2003 |
| WO | WO 2005/018426 A2 | 3/2005 |
| WO | WO 2007/121747 A1 | 11/2007 |
| WO | WO 2008/045744 A2 | 4/2008 |
| WO | WO 2008/093313 A1 | 8/2008 |

OTHER PUBLICATIONS

European Search Report corresponding to European Application No. EP 06 00 4113, completed Jun. 13, 2006; 2 pages.

European Search Report corresponding to European Application No. EP 06 00 6537, completed Jun. 16, 2006; 2 pages.

International Search Report corresponding to International Application No. PCT/US03/12894, completed Nov. 7, 2003; mailed Nov. 17, 2003; 3 pages.

European Search Report corresponding to European Application No. EP 10 25 0629, completed Jun. 28, 2010; mailed Jul. 6, 2010; 3 pages.

\* cited by examiner

ARTICULATING SURGICAL PORTAL APPARATUS WITH SPRING

CROSS-REFERENCE TO RELATED APPLICATION(S)

This patent application claims priority to and the benefit of U.S. Provisional Patent Application No. 61/163,490, filed in the U.S. Patent and Trademark Office on Mar. 26, 2009.

BACKGROUND

1. Technical Field

The present disclosure relates to a surgical portal apparatus adapted to permit the introduction of surgical instrumentation into a patient's body. In particular, the present disclosure relates to a surgical portal apparatus including an articulating valve system adapted to receive an instrument in sealing engagement therewith.

2. Description of the Related Art

Minimally invasive and laparoscopic procedures generally require that any instrumentation inserted into the body is sealed, i.e., provisions must be made to ensure that gases and/or fluids do not enter or exit the body through an endoscopic incision, such as, for example in surgical procedures where the surgical region is insufflated. For such procedure, the introduction of a tube into anatomical cavities, such as the peritoneal cavity, is usually accomplished by use of a system incorporating a trocar and cannula assembly. Since the cannula is in direct communication with the interior of the peritoneal cavity, insertion of the cannula into an opening in the patient's body to reach the inner abdominal cavity should be adapted to maintain a fluid tight interface between the abdominal cavity and the outside atmosphere. In view of the need to maintain the atmospheric integrity of the inner area of the cavity, a seal assembly for a cannula, which permits introduction of a wide range of surgical instrumentation and maintains the atmospheric integrity of the inner area of the cavity is desirable. In this regard, there have been a number of attempts in the prior art to achieve such sealing requirements. A difficulty encountered with conventional seal assemblies, however, is the inability of accommodating the wide range of sizes of instrumentation. In addition, angulation and/or manipulation of instrumentation within the cannula often present difficulties with respect to maintaining seal integrity.

SUMMARY

Accordingly, the present disclosure is directed to a surgical portal apparatus which includes a housing and a portal member. The portal member is connected to the housing and extends therefrom. The portal member also defines a longitudinal axis, which includes a longitudinal passageway that permits a passage for a surgical object to be inserted therethrough.

A seal mount is mounted to the housing and has an internal or object seal which is secured by a seal cap to establish a substantial sealed relation with the surgical object. The seal mount is articulated relative to the housing between a first position and a second position. A biasing member, (e.g., a spring), is mounted within the seal mount for biasing, (i.e., returning), the seal mount toward the first position relative to the housing.

The seal mount includes an articulating segment defining an arcuate surface that cooperates with a corresponding surface of the housing to facilitate articulating movement of the seal mount upon offset manipulation of the surgical object. The housing defines an outer arcuate surface that cooperates with a corresponding surface of the seal mount during offset manipulation of the surgical object. The housing also defines a first axis and the seal mount defines a second axis, where the first axis and the second axis is in general alignment at the first position.

The seal mount further includes an enclosure segment operatively connected to the articulation segment and engages the spring member to facilitate mounting of the spring member relative to the seal mount.

Additionally, a closure valve is mounted between the seal housing and the base housing, where the closure valve is adapted to substantially close the longitudinal passageway in the absence of a surgical object.

In embodiments, the seal cap and the seal mount may be connected by a bayonet-type fitting, a threaded fitting, a snap fitting, a glue fitting, or a weld fitting. In the same manner, the enclosure segment and the articulating segment may be connected by the above-mentioned connections.

BRIEF DESCRIPTION OF THE DRAWINGS

The foregoing features of the present disclosure will become more readily apparent and will be better understood by referring to the following detailed description of embodiments, which are described hereinbelow with reference to the drawings wherein.

DETAILED DESCRIPTION

Figure 1:
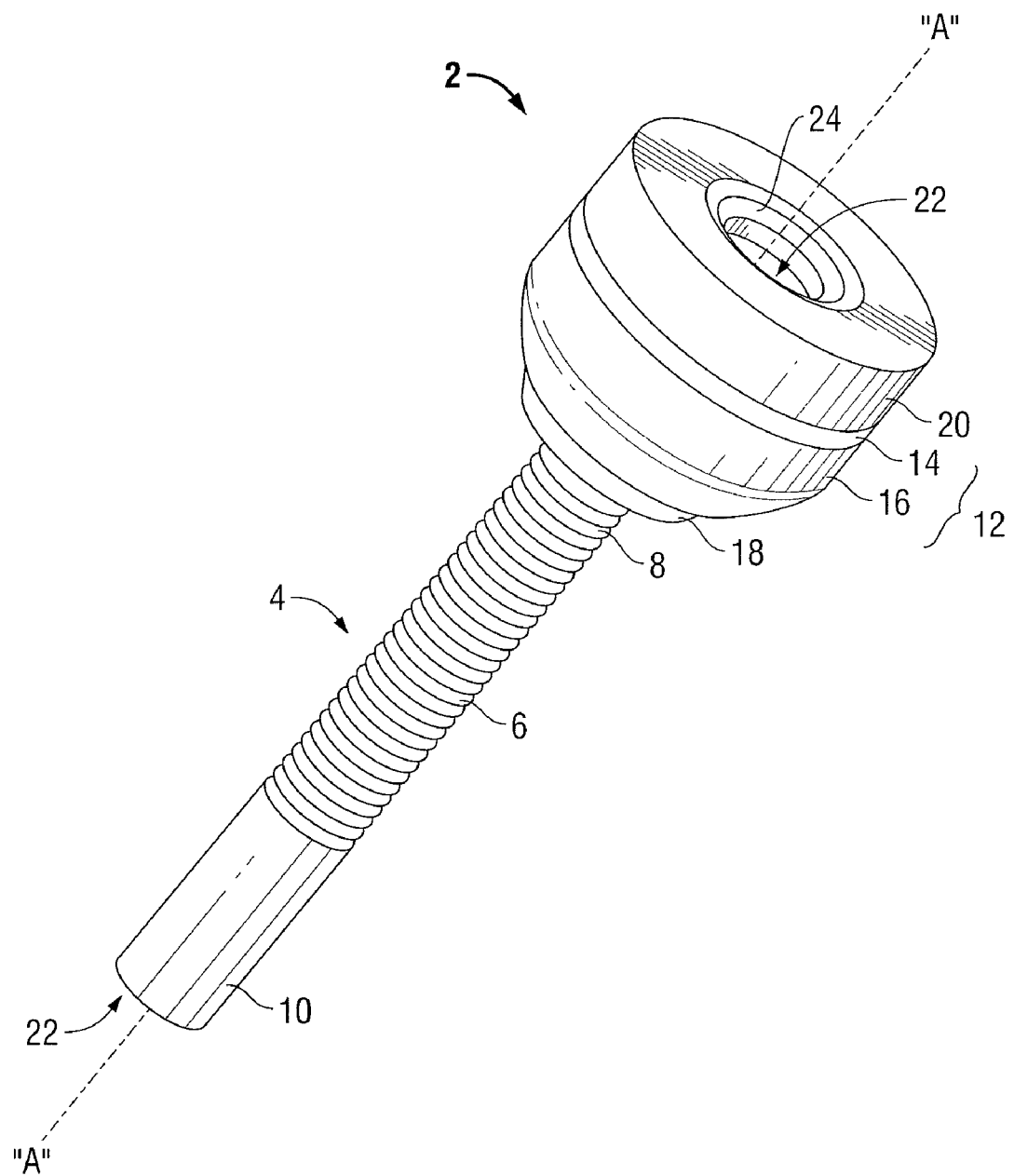
FIG. 1 is a perspective view of a surgical portal apparatus in accordance with the principles of the present disclosure.

A surgical portal apparatus 2 of the present disclosure provides access to underlying body tissue and also provides a substantial seal between a body cavity of a patient and the outside atmosphere before, during, and after insertion of an instrument. Moreover, the portal apparatus 2 of the present disclosure is capable of accommodating instruments of varying diameters, e.g., from 5 mm to 15 mm, by providing a substantially air tight seal when a surgical instrument is inserted therethrough. The present surgical portal apparatus allows a user, during endoscopic surgery, to utilize a variety of instruments having different diameters, which are often needed during a single surgical procedure. The surgical portal apparatus also provides various positions for the user to angulate the instrument within the body cavity of the patient by manipulating the instrument and a seal mount.

The portal apparatus 2 incorporates a seal adapted for the introduction and manipulation of various types and sizes of instruments while maintaining a fluid tight interface about the instrumentation to preserve the atmospheric integrity of a surgical procedure from gas and/or fluid leakage. Specifically, the seal mount accommodates angular manipulation of the surgical instrument relative to the longitudinal axis of the portal apparatus. This feature of the present disclosure minimizes the stress put on the seal as the instrument is manipulated by the user. Examples of instrumentation include clip appliers, graspers, dissectors, retractors, staplers, laser probes, photographic devices, endoscopes and laparoscopes, tubes, and the like. Such instruments will be collectively referred to herein as "instruments or instrumentation".

In the following description, as is traditional, the term "proximal" refers to the portion of the instrument closest to the user, while the term "distal" refers to the portion of the instrument farthest from the user.

Referring now to the drawings, in which like reference numerals identify identical or substantially similar parts throughout the several views, the figures illustrate the surgical portal apparatus 2 of the present disclosure. Portal apparatus 2 may be adapted for use as a cannula suitable for the intended purpose of accessing a body cavity, for example, the abdominal cavity, and permit introduction of instruments therethrough. As an alternate embodiment, portal apparatus 2 may be adapted to receive the hand and possibly the arm of the surgeon during a minimally invasive procedure where hand access is desired. Portal apparatus 2 is particularly adapted for use in laparoscopic surgery where the peritoneal cavity of the patient is insufflated with a suitable gas, e.g., $CO_2$, to raise the cavity wall from the internal organs therein. Portal apparatus 2 is typically used with an obturator assembly (not shown) which is a sharp pointed instrument positionable within the passageway of the portal apparatus 2. The obturator assembly is utilized to penetrate the abdominal wall and then subsequently removed from the portal apparatus to permit introduction of the surgical instrumentation utilized to perform the procedure.

Referring now to FIG. 1, a portal apparatus 2 is illustrated having a portal member 4, a seal mount 12 and a seal cap 20. The seal mount 12 and its components will be discussed in further detail below. The portal member 4 includes a portal sleeve 6 having a proximal end 8 and distal end 10, where a seal housing 18 is attached to the proximal end 8 of portal sleeve 6 by conventional means or may be integrally bound with sleeve 6. The portal sleeve 6 defines a longitudinal axis "A" extending along the length of sleeve 6 and further defines an internal longitudinal passage 22 dimensioned to permit passage of surgical instrumentation. The sleeve 6 may be formed of stainless steel or any other suitable rigid material such as a polymeric material titanium, or the like. The sleeve 6 may also be configured to be clear or opaque to allow the user to monitor the instrument as it is being inserted and/or removed through the portal member 4. The diameter of sleeve 6 may vary, but typically ranges from 10 to 15 mm for use with the seal housing 18 of the present disclosure.

Figure 2:
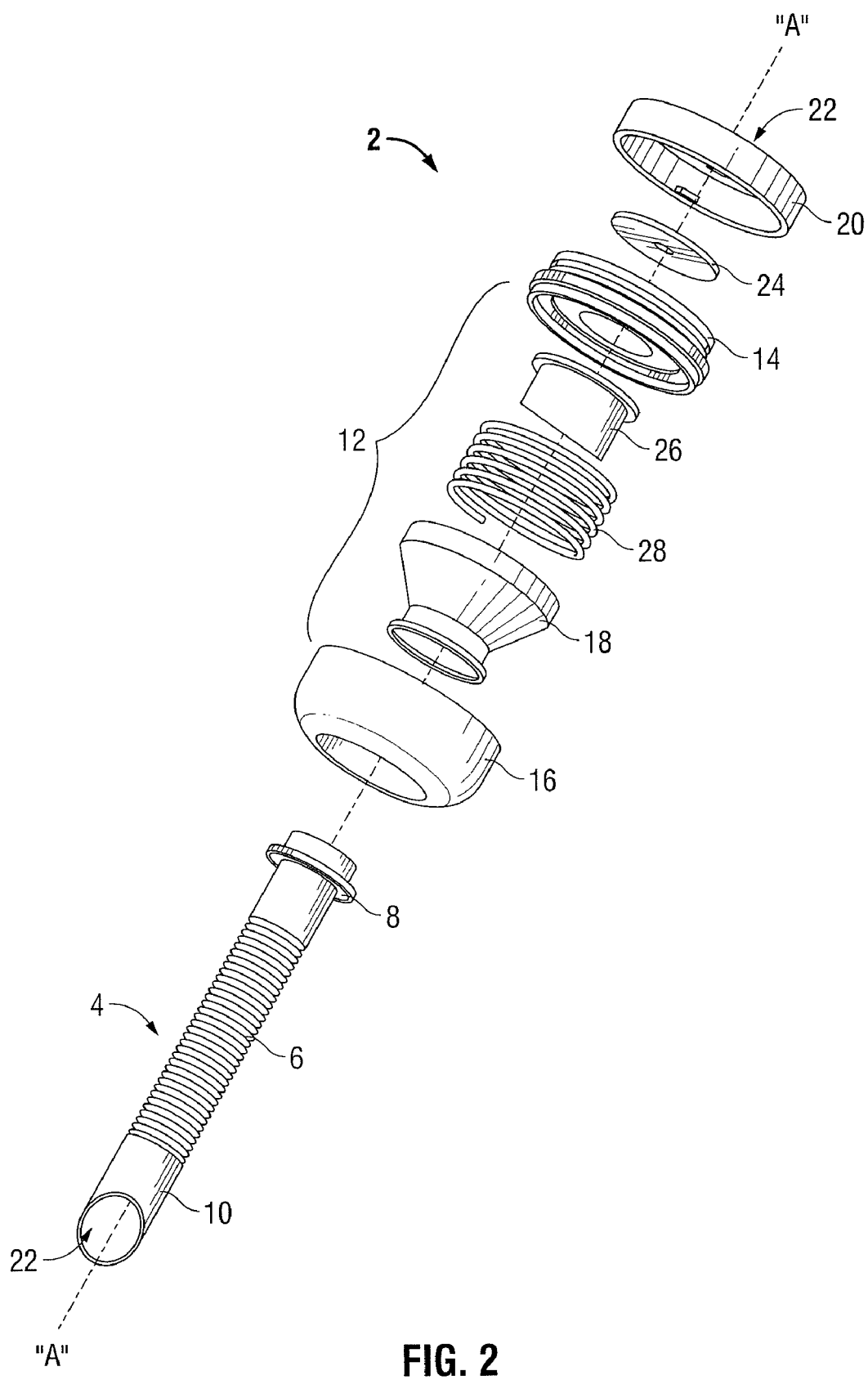
FIG. 2 is a perspective view with parts separated of the portal apparatus.

Turning now to FIG. 2, a perspective view is depicted with parts of portal apparatus 2 separated. The seal cap 20 is configured to attach on the proximal portion of seal mount 12, which is also referred to as an enclosure segment 14 to secure and contain an object seal 24. The seal mount 12 provides for mounting object seal 24 and to facilitate in maneuvering object seal 24 over the housing 18.

Figure 3:
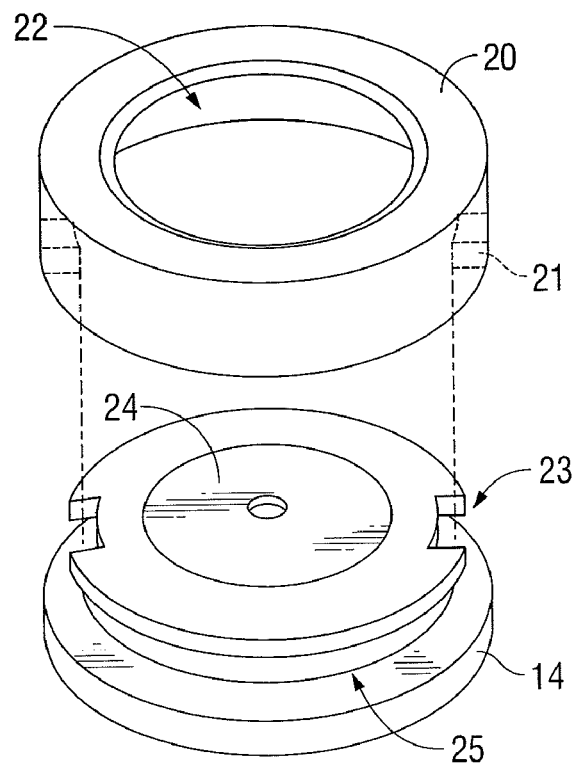
FIG. 3 is a perspective view of a seal cap and seal mount of the portal apparatus of FIG. 1.

As depicted in FIG. 3, seal cap 20 is secured onto the enclosure segment of seal mount 12 by a bayonet-type fitting. The enclosure segment 14 defines an inner channel 25 alongside the perimeter and also having grooves 23. Seal cap comprises a plurality of tabs 21, which are defined on the inner lip of seal cap 20. As the seal cap 20 is placed on the enclosure segment 14, the tabs 21 are configured and dimensioned to pass through the grooves 23 of enclosure segment 14. When seal cap 20 is placed into grooves 23, seal cap may be rotated, in either a clockwise or counter-clockwise direction, where tabs 21 are guided within the inner channel 25. The inner channel 25 of enclosure segment 14 may also have a slight incline to guide tabs 21 along the inner channel 25. As tabs 21 move along the inner channel 25, a frictional force may be exerted towards tabs 21, thus creating a secure seal towards object seal 24. In embodiments, seal cap 20 may be connected to seal mount 12 by any conventional technique including a snap fit arrangement, threaded coupling, clamp coupling, bayonet coupling, etc.

During a surgical procedure, the user may require to use a different type and/or sized surgical instrument. When a situation such as this occurs, the user may remove the seal cap 20 from the portal apparatus 2 and replace the existing object seal 24 with a different sized object seal. By replacing only the object seal, the user may safely and effectively use a different type sized surgical instrument, without the need of replacing portal apparatus 2 with a different type and/or sized portal apparatus.

Figure 6B:
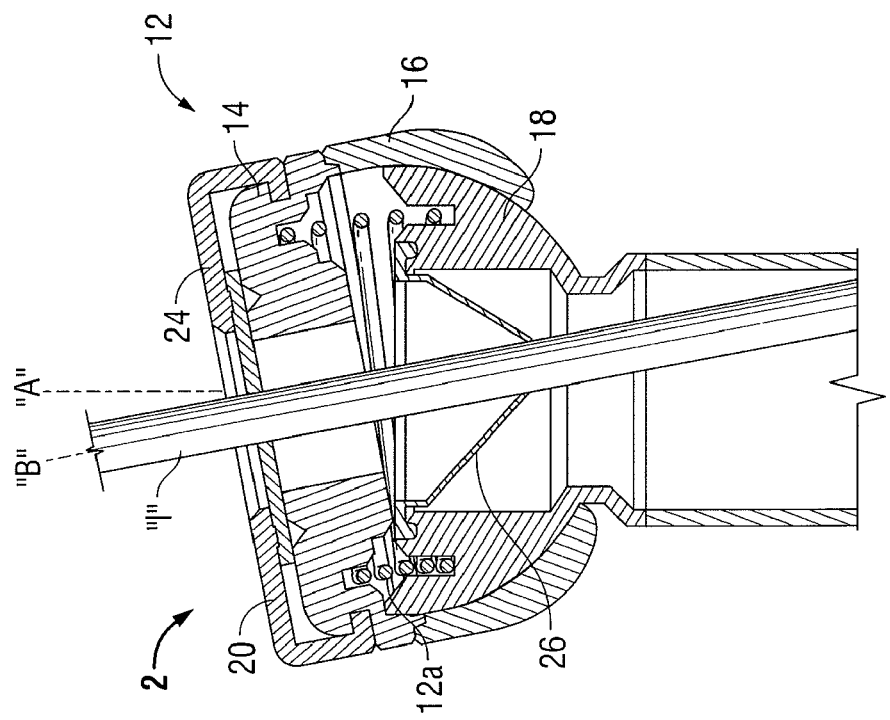
FIG. 6B is a side cross-sectional view of the seal mount of FIG. 1 showing the surgical object in a second position.
Figure 6A:
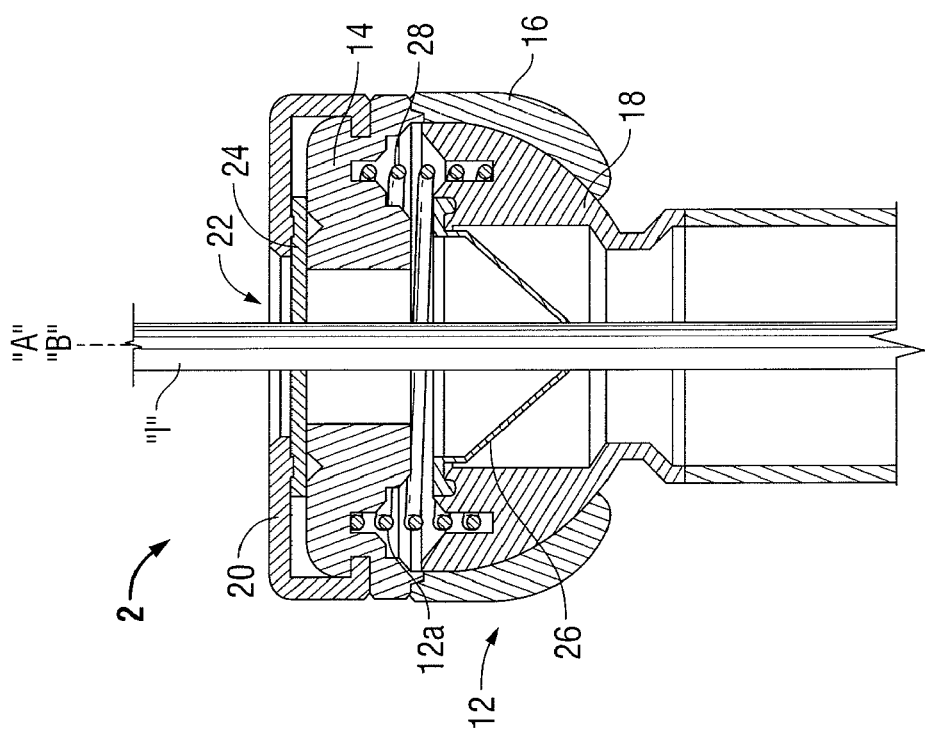
FIG. 6A is a side cross-sectional view of the seal mount of FIG. 1 showing a surgical object in a first position.

Additionally, in accordance with the present disclosure, object seal 24 may be constructed from a rubber or any other suitable elastomeric material contemplated in the art. As mentioned above, the longitudinal passageway 22 of object seal 24 may vary in size depending on the types of instruments being utilized. During the surgical procedure, the object seal 24 is configured to minimize the loss of insufflated gasses through portal member 4 by forming a substantial seal about surgical object "I", e.g., surgical instrument, as shown in FIGS. 6A and 6B.

Figure 4:
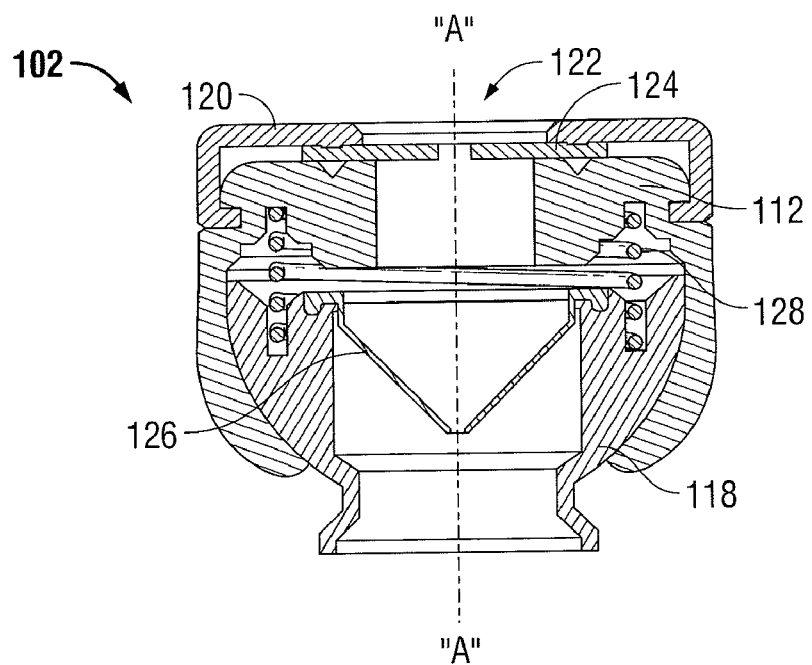
FIG. 4 is a side cross-sectional view of an alternate embodiment of a seal mount of a portal apparatus.

Turning now to FIG. 4, another embodiment of a portal apparatus 102 having a seal mount 112 is configured in a one-piece design. The seal mount 112 includes a seal cap 120, an object seal 124, a biasing member 128, and a zero-closure valve 126, as similarly shown in portal apparatus 2. The seal cap 120 and the object seal 124 are secured onto seal mount 112 in a similar fashion as mentioned above with respect to portal apparatus 2. The one-piece seal mount 112 may be constructed from an elastic material to allow the articulating segment of seal mount 112 to expand over seal housing 118, thus allowing seal mount 112 to have substantially similar manipulative properties as seal mount 12, which will be described in detail below.

Referring back to FIG. 2, the enclosure segment 14 of seal mount 12 facilitates to the securement of closure valve on to housing 18. Articulating segment 16 is configured in a cup-shaped design and is constructed from any suitable material or combinations of materials (e.g., metal or plastic, polyurethane, etc). The articulating segment 16 of seal mount 12 includes a spherical internal surface to provide a rotational swiveling motion around the bottom portion of housing 18.

The seal mount 12 also includes a biasing member 28 which is contained within the enclosure segment 14 and the articulating segment 16, where both segments define a biasing member channel 12a. The biasing member 28, (e.g., a spring) helps to facilitate in restoring seal mount 12 to return to a first position, which is a flat, normally perpendicular position with respect to housing 18. As shown in FIGS. 6A and 6B, the biasing member 28 provides a comfortable, flexible and resistive motion thus allowing the seal mount 12 to be articulated about housing 18 by a user to any second position, defining the "B" axis. The seal mount 12 is adapted to return back to the first position relative to the housing 18, which is along the "A" axis, upon the user selecting the surgical instrument "I".

FIG. 2 also illustrates a zero-closure valve 26 enclosed and situated within enclosure segment 14 and housing 18. Zero-closure valve sits on housing 18, while enclosure segment 14 facilitates securement to zero-closure valve 26. Closure valve 26 may be a duck bill valve, which tapers distally and inwardly to a sealed configuration as shown in the figure. Valve 26 opens to permit passage of the surgical instrumentation and closes in the absence of the instrumentation "I". The valve 26 is adapted to close upon exposure to the forces exerted by the insufflation gases in the internal cavity. Other zero closure valves are also contemplated including single or multiple slit valve arrangements, trumpet valves, flapper valves, etc.

Figure 5A:
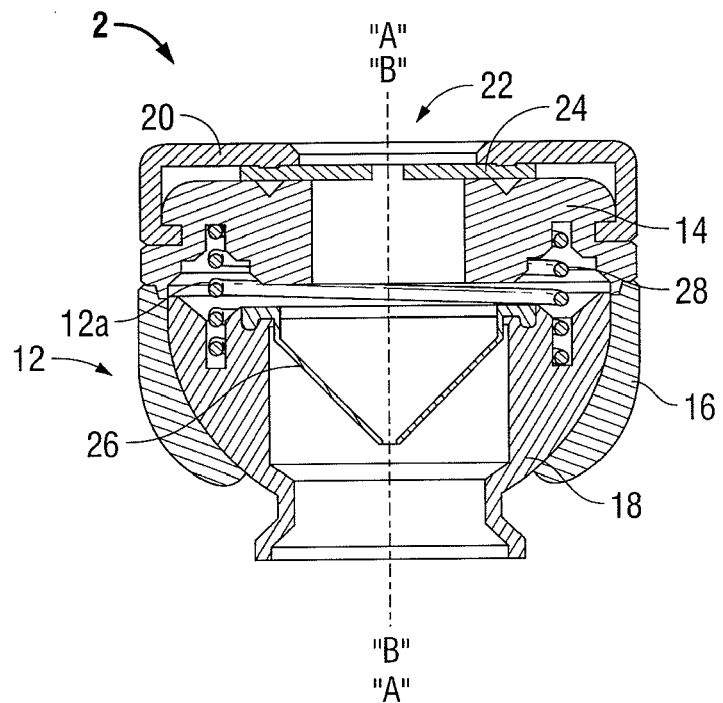
FIG. 5A is a side cross-sectional view of the seal mount of FIG. 1 showing the seal mount in a first position.
Figure 5B:
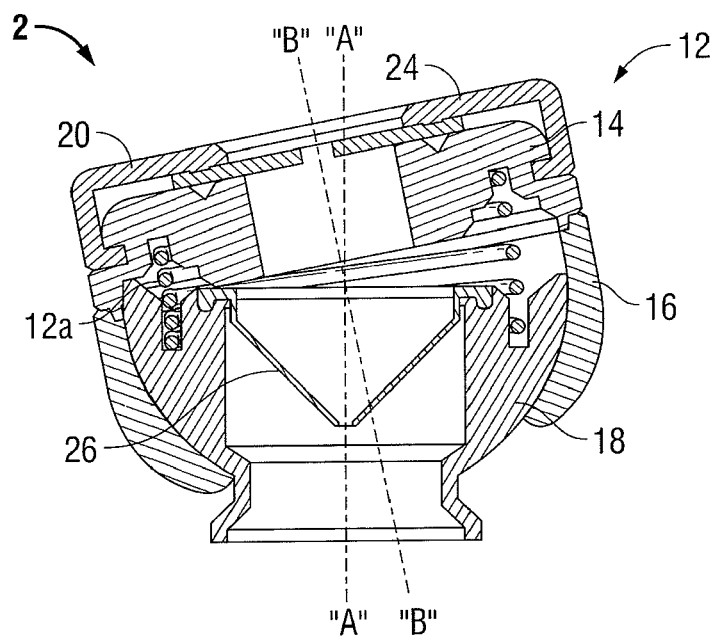
FIG. 5B is a side cross-sectional view of the seal mount of FIG. 1 showing the seal mount in a second position.

FIGS. 5A and 5B illustrates a side cross-sectional view of portal apparatus 2, further illustrating the seal mount 12 in first and second positions. Both housing 18 and seal mount 12 contain longitudinal passageways, axis "A" and variable axis "B", respectively. When both housing 18 and seal mount 12 are in the first position, (i.e., aligned with each other), the instrument "I" passes through seal mount 12 and housing 18, thus passing through both longitudinal passageways "A" and "B". Housing 18 is in a fixed position relative to the portal apparatus 2. However, seal mount 12 is not fixed in one position, as mentioned above, and is movable about housing 18. Movement of the seal mount 12 is provided by articulating segment 16 of seal mount 12 having an arcuate surface. The inner arcuate surface of seal mount 12 cooperates with the outer arcuate surface of housing 18 to facilitate articulating movement of seal mount 12 upon any offset manipulation of instrument "I", shown in FIG. 6A.

As shown in FIG. 6B, seal mount 12 may be moved to a second position, along the variable "B" axis, which may be anywhere articulating member 16 may rotate and swivel around housing 18. When seal mount 12 is in a first position, seal mount 12 and housing 18 are in alignment with each other, thus axis "A" and axis "B" are in alignment with each other. When seal mount 12 is in a second position, seal mount 12 and housing 18 are not in alignment, thus the position of axis "B" varies and is not in alignment with axis "A".

As shown in FIGS. 6A and 6B, instrument "I" passes further distally into seal mount 18, passing through zero closure valve 26 and portal sleeve 6 and into the body cavity of a patient (not shown). The above-mentioned articulation, allows the user to easily manipulate instrument "I", without adding substantial stress to the internal seals of portal apparatus 2, since the seal mount 12 is configured to substantially move about axis "B" along with instrument "I".

While the invention has been particularly shown, and described with reference to the embodiments, it will be understood by those skilled in the art that various modifications and changes in form and detail may be made therein without departing from the scope and spirit of the invention. Accordingly, modifications such as those suggested above, but not limited thereto, are to be considered within the scope of the invention.

What is claimed is:

1. A surgical portal apparatus, which comprises:
 a housing having an outer surface;
 a portal member connected to the housing and extending therefrom, the portal member defining a longitudinal axis and having a longitudinal passageway for permitting passage of a surgical object;
 a seal mount being secured to the housing and articulable relative to the housing between articulated and unarticulated positions, the seal mount including an enclosure segment, and an articulating segment, the enclosure segment and the articulating segment supporting a biasing member that facilitates the movement of the seal mount to the unarticulated position, the articulating segment including an internal surface with an arcuate portion that engages the outer surface of the housing to facilitate articulating movement of seal mount relative to the housing; and
 a seal cap secured to the enclosure segment of the seal mount, the enclosure segment supported between the seal cap and the housing.

2. The surgical portal apparatus according to claim 1, wherein the biasing member is a spring, the spring being engageable with the housing and the seal mount.

3. The surgical portal apparatus according to claim 1, wherein the seal cap and the enclosure segment of the seal mount are releasably connected.

4. The surgical portal apparatus according to claim 1, wherein the housing includes a closure valve, the closure valve adapted to substantially close the longitudinal passageway in the absence of a surgical object.

5. The surgical portal apparatus according to claim 1, wherein the housing defines a first axis and the seal mount defines a second axis, the first axis and the second axis being in general alignment in the unarticulated position of the seal mount.

6. The surgical portal apparatus according to claim 1, wherein the arcuate portion of the internal surface of the articulating segment remains in contact with the outer surface of the housing during offset manipulation of the surgical object.

7. The surgical portal apparatus according to claim 1, wherein the outer surface of the housing defines a first radius of curvature and the internal surface of the articulating segment defines a second radius of curvature, wherein the first and second radii of curvature are substantially similar.

8. The surgical portal apparatus according to claim 1, wherein the enclosure segment supports an object seal.

9. A surgical portal apparatus, which comprises:
 a housing having an outer surface;
 a portal member connected to the housing and extending therefrom, the portal member defining a longitudinal axis and having a longitudinal passageway for permitting passage of a surgical object;
 a seal mount being secured to the housing and articulable relative to the housing between articulated and unarticulated positions, the seal mount including an enclosure segment, and an articulating segment, the enclosure segment and the articulating segment supporting a biasing member that facilitates the movement of the seal mount to the unarticulated position, the articulating segment including an internal surface with an arcuate portion that engages the outer surface of the housing to facilitate articulating movement of seal mount relative to the housing, wherein the arcuate portion of the internal surface of the articulating segment is substantially spherical and the outer surface of the housing is substantially spherical to enable the seal mount to rotationally swivel about the housing.

10. The surgical portal apparatus according to claim 9, wherein the biasing member is a spring, the spring being engageable with the housing and the seal mount.

11. The surgical portal apparatus according to claim 9, wherein the housing includes a closure valve, the closure valve adapted to substantially close the longitudinal passageway in the absence of a surgical object.

12. The surgical portal apparatus according to claim 9, wherein the housing defines a first axis and the seal mount defines a second axis, the first axis and the second axis being in general alignment in the unarticulated position of the seal mount.

13. The surgical portal apparatus according to claim 9, wherein the arcuate portion of the internal surface of the articulating segment remains in contact with the outer surface of the housing during offset manipulation of the surgical object.

14. The surgical portal apparatus according to claim 9, wherein the outer surface of the housing defines a first radius of curvature and the internal surface of the articulating segment defines a second radius of curvature, wherein the first and second radii of curvature are substantially similar.

15. The surgical portal apparatus according to claim 9, wherein the enclosure segment supports an object seal.

16. The surgical portal apparatus according to claim 9, further comprising a seal cap secured to the seal mount.

* * * * *